US010342693B1

United States Patent
Dimmitt et al.

(10) Patent No.: US 10,342,693 B1
(45) Date of Patent: Jul. 9, 2019

(54) CHIN-STRAP FOR TUBING RETENTION

(71) Applicant: Neotech Products, Inc., Valencia, CA (US)

(72) Inventors: Sara J. Dimmitt, Palmdale, CA (US); Craig R. McCrary, Valencia, CA (US)

(73) Assignee: Neotech Products LLC, Valencia, CA (US)

( * ) Notice: Subject to any disclaimer, the term of this patent is extended or adjusted under 35 U.S.C. 154(b) by 49 days.

(21) Appl. No.: 13/986,018

(22) Filed: Mar. 25, 2013

(51) Int. Cl.
*A61C 7/06* (2006.01)
*A61F 5/37* (2006.01)

(52) U.S. Cl.
CPC .............. *A61F 5/3707* (2013.01); *A61C 7/06* (2013.01)

(58) Field of Classification Search
CPC .............. A61F 5/56; A61C 7/06; A61C 7/065
USPC ..... 128/846, 848, 857, 876, 201.22, 207.17; 606/201, 204.15, 204.25, 204.35; 27/25.1; 602/17, 74
See application file for complete search history.

(56) References Cited

U.S. PATENT DOCUMENTS

| | | | |
|---|---|---|---|
| 3,741,202 A * | 6/1973 | Morgan | A61F 13/122 128/DIG. 15 |
| D410,021 S | 5/1999 | Heyman et al. | |
| 6,126,683 A * | 10/2000 | Momtaheni | A61F 5/34 602/13 |
| 6,279,577 B1 * | 8/2001 | Savaiano | 128/848 |
| 6,656,143 B2 * | 12/2003 | Browd | A61F 5/3707 602/13 |
| 7,000,615 B2 * | 2/2006 | Taylor-Kennedy | 128/857 |
| 2004/0187873 A1 * | 9/2004 | Brown | 128/848 |
| 2006/0106330 A1 * | 5/2006 | Andrade et al. | 602/74 |

* cited by examiner

*Primary Examiner* — Keri J Nelson
(74) *Attorney, Agent, or Firm* — Kelley & Kelley, LLP

(57) ABSTRACT

A chin support for an infant comprising thin, flexible support sections applicable to infant facial zones spaced below the ears, first flexible support straps extending sidewardly between the support sections between and over upper and lower chin zones, below mouth level, and second flexible support straps extending upwardly and rearwardly of ear zones and to upper head zones, for chin retention, with balanced force exertion, there being a crescent shape gap.

13 Claims, 2 Drawing Sheets

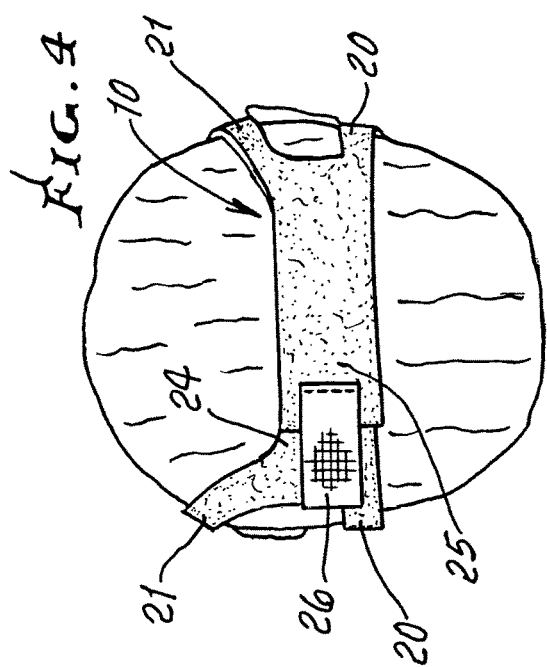
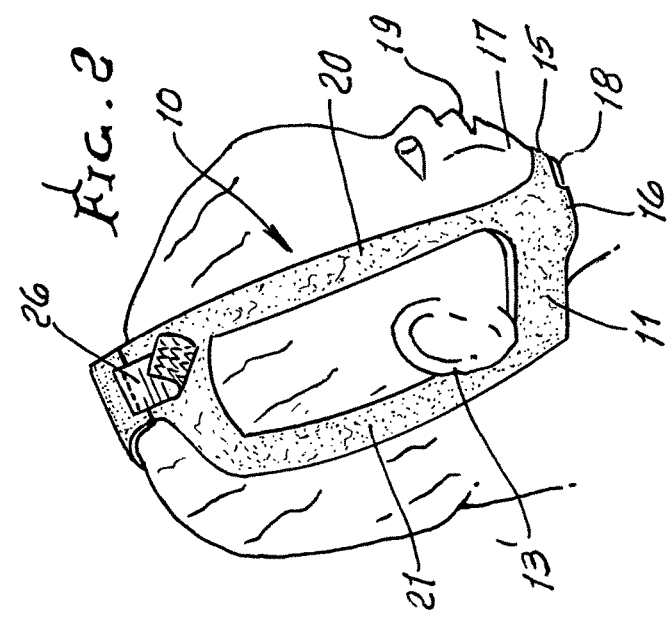
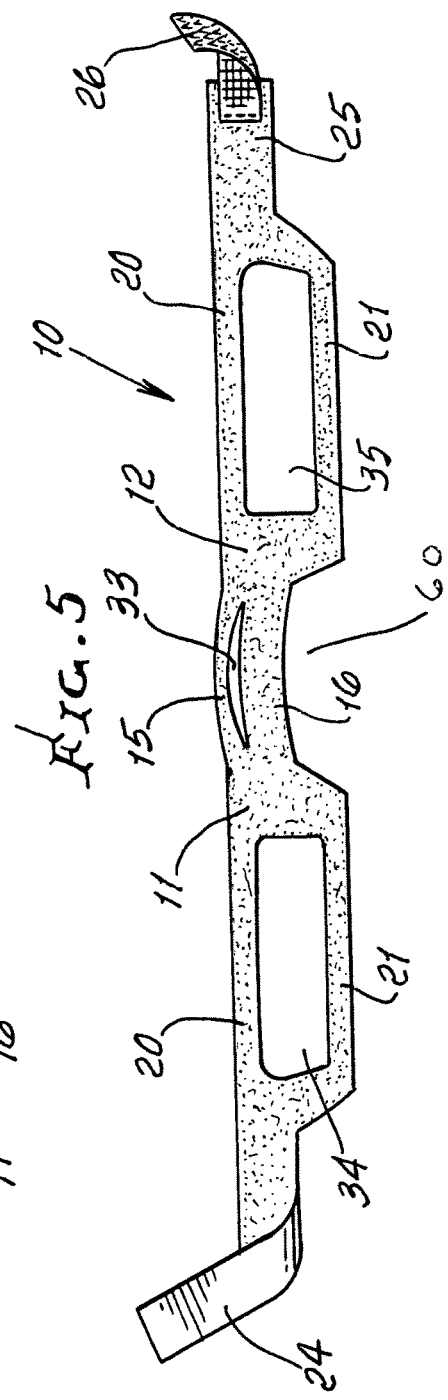

CHIN-STRAP FOR TUBING RETENTION

BACKGROUND OF THE INVENTION

Continuous positive airway pressure is a common modality for delivering oxygen therapy to the newborn via a nasal interface. While these patients can breathe spontaneously, their lungs are not developed enough to maintain the patency of the terminal air sacs. Since newborns tend to breathe through an open mouth, flow/pressure is lost from the oropharnynx. To overcome this defect chin support is needed so that the mouth is maintaining the closed position. A simple, compact, easily usable device is needed to achieve this objection.

There is need for apparatus as referred to, and particularly positioning and adjusting means, whereby the infant's chin is safely retained in mouth closing position. There is also need for such apparatus which does not slide back and forth on the infant's chin or neck, and which is easily adjustable to accommodate to various head sizes and shapes, and which provides additional advantages, as will appear.

SUMMARY OF THE INVENTION

It is a major object of the invention to provide highly advantageous apparatus as referred to. Basically, the apparatus provides chin support means for an infant comprising:

a) thin, flexible support sections applicable to infant facial zones spaced below the ears, b) first flexible support straps extending sidewardly between the support sections between and over upper and lower chin zones, below mouth level, c) second flexible support straps extending upwardly from the support sections forwardly and rearwardly of ear zones and to upper head zones, for chin retention.

It is another object to provide first support straps that include an upper strap portion extending with curvature adjacent the chin zone directly below the infant's lower lip zone.

A further object is to provide the first support straps to include a lower strap portion extending with cupping configuration adjacent the underside of the chin zone.

Yet another object is to provide two sets of the second support straps, respectively associated with the infant's two ears, together with means to interconnect uppermost extents of the second support straps at infant's head top level. In particular, such second strap uppermost extents merge into overlapping retention at the top head zone of the infant.

The invention also includes provision of a support as described and that consists of soft, flexible material, having substantially uniform thickness throughout support extent.

As will be seen, the chin support has a flat plane extended position, wherein said first flexible support straps merge longitudinally endwise with said thin flexible support section, at locations longitudinally endwise beyond a laterally narrow longitudinally elongated gap formed between said first flexible support straps.

Also, each of the thin flexible support sections has overall lateral widths substantially greater the combined lateral widths of said first flexible support straps and gap.

Further, two longitudinally elongated openings are formed by said chin support, each opening partially bounded by two of said second flexible support straps.

These and other objects and advantages of the invention, as well as the details of an illustrative embodiment, will be more fully understood from the following specification and drawings, in which:

DRAWING DESCRIPTION

FIG. 2 is a side view of the support apparatus as applied to an infant's head;

FIG. 4 is a top plan view of the apparatus, as viewed toward head top, and FIG. 5 shows the FIGS. 1-4 apparatus in extended condition, in a flat plane.

DETAILED DESCRIPTION

Figure 1:
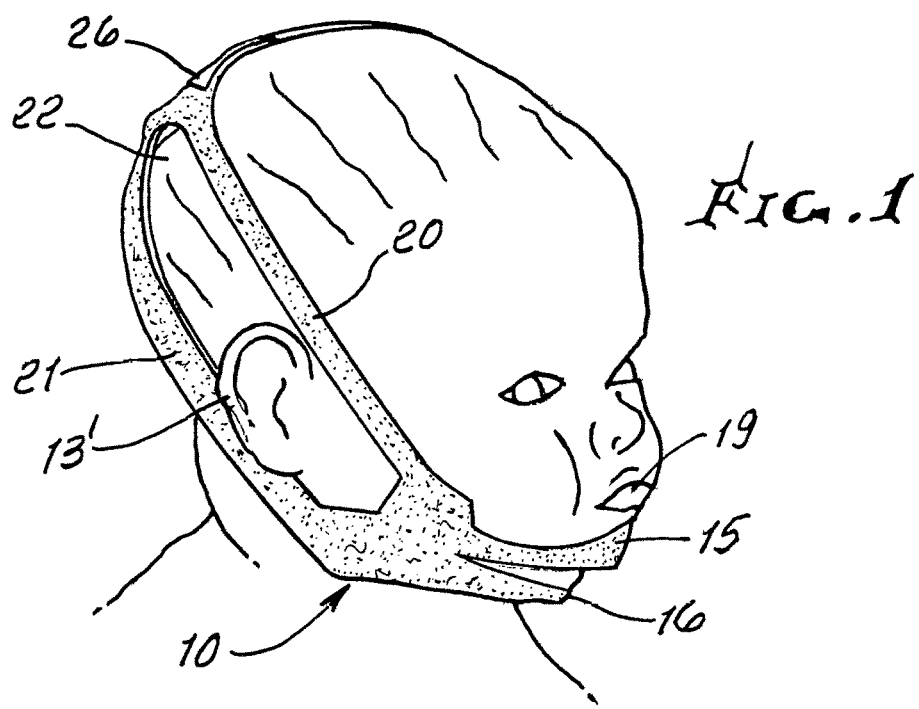
FIG. 1 is a perspective view of strap apparatus applied to an infant's head and showing its relation to an infant's chin and right ear.
Figure 3:
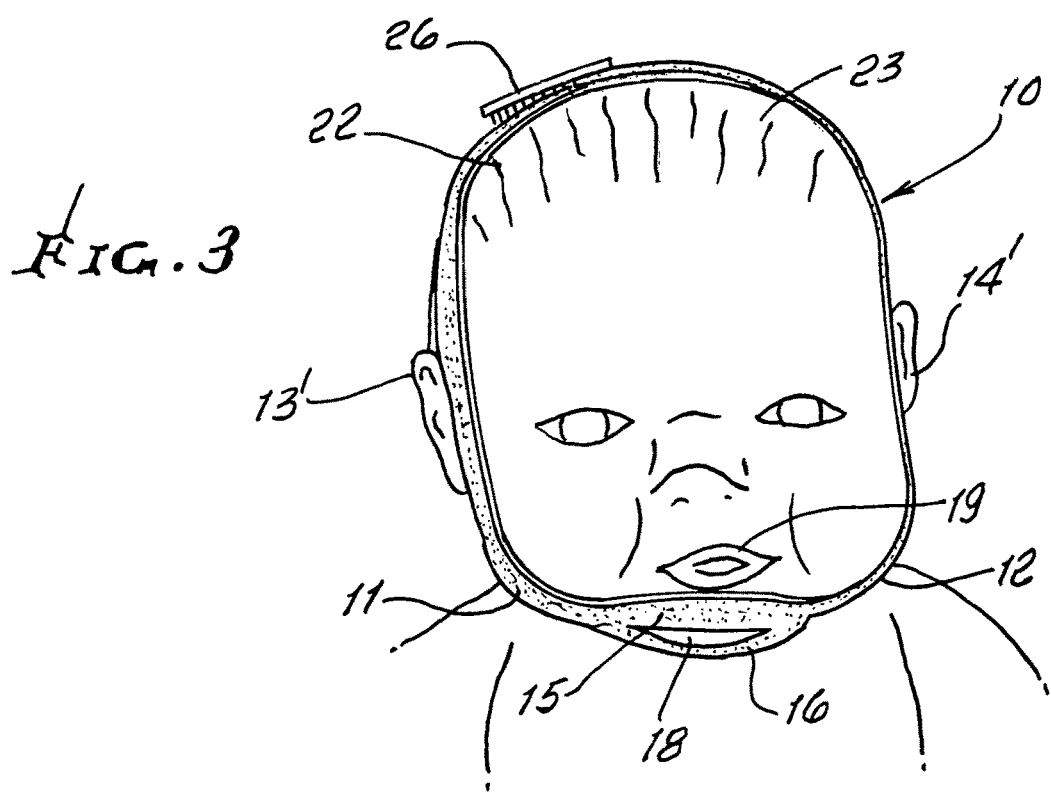
FIG. 3 is a frontal view of the FIGS. 1 and 2 support apparatus.

Basically, the non-invasive apparatus 10 of the invention as seen in in FIGS. 1-4, provides chin support means for an infant comprising:

a) thin left and right flexible support sections 11 and 12 applicable to infant facial zones spaced below the ears 13' and 14', b) first flexible support straps 15 and 16 extending sidewardly or laterally between the support sections, between and over upper and lower chin zones 17 and 18, below mouth 19 level, c) and second flexible support straps 20 and 21 extending upwardly from the support sections 11 and 12 forwardly and rearwardly of ears or ear zones, and to upper head zones 22 and 23, for chin retention, holding the mouth closed, by holding the chin up.

There are typically two pairs of straps 20 and 21, i.e. one pair at one side of the head, and a second pair at the opposite side of the head.

Adhesive tape 26 or VELCRO is applied to one or both end extents 24 and 25, to hold the tensioned straps upwardly, holding the mouth closed.

Accordingly, the ears and ear zones are not engaged by or covered by the straps 20 and 21, nor is the infant's mouth covered by straps 15 and 16, whereby the retention apparatus extends non-invasively, smoothly and comfortably adjacent the infant's head, in retaining relation to the chin support, while the infant's head is moved about.

Note further that strap 15, or portion, extends with spaced curvature and cupping, relative to and adjacent the chin recessed zone directly below the infant's lower lip, preventing strap coverage of the lower lip. Note also that straps 15 and 16 are substantially shorter than the second straps 20 and 21, to locate support sections or pads 11 and 12 substantially below and in non-interfering relation with the ears.

Each of the two sets of second support straps 20 and 21 has uppermost extent that merges with a single top strap associated with the head of the infant. The straps and pads typically consist of thin (i.e. less than ⅛ inch uniform thickness) soft, flexible material, for comfort, and to provide a compact, comfortable, simple and non-invasive apparatus.

Further advantages include:

breathable, and wicks perspiration split chin strapping (for chin straddling, comfort and stability)

resists support and strap sliding on infant's neck open areas around infant ears prevents folding over and possibility of ulcers or necrosis adapts well to different head sizes latex/phthalate free Referring to FIG. 5, the chin support has a flat plane extended position, wherein said first flexible support straps merge longitudinally endwise with said thin flexible support sections, at locations longitudinally endwise beyond a laterally narrow longitudinally elongated crescent shaped gap 33 formed between said first flexible support straps.

Also, each of the thin flexible support sections has overall lateral width substantially greater than the combined lateral widths of said first flexible support straps and gap 33.

Further, two longitudinally elongated openings 34 and 35 are formed by said chin support, each opening partially bounded by two of said second flexible support straps.

Second gap 60 extends between support sections 11 and 12 and adjacent 16.

We claim:

1. A chin support for an infant comprising
    a) thin, flexible support sections applicable to infant facial zones spaced below the ears when the chin support is worn,
    b) first flexible support straps adapted to extend sidewardly between said support sections between and over upper and lower chin zones, below mouth level when the chin support is worn,
    c) second flexible support straps adapted to extend upwardly from said support sections and above ear zones and to upper head zones when the chin support is worn, for chin retention,
    d) and wherein the chin support has a flat plane extended position, wherein said first flexible support straps merge longitudinally endwise with said thin flexible support sections, at locations longitudinally endwise beyond a laterally narrow longitudinally elongated slit-shaped first gap formed between said first flexible support straps, said first gap tapering endwise toward both said first flexible support sections,
    e) said first straps include an upper strap portion adapted to extend with curvature adjacent the chin zone directly below the infant's lower lip zone when the chin support is worn,
    f) at least one of the first flexible support straps includes a lower strap portion adapted to extend with cupping configuration adjacent the underside of the infant's chin zone when the chin support is worn,
    g) said first gap having a crescent configuration,
    h) there being a second gap formed between said thin flexible support sections adjacent to the lower strap portion,
    i) a first of said thin flexible support sections located adjacent one end of said second gap, and a second of said thin flexible support sections located adjacent an opposite end of said second gap,
    j) each of said flexible support sections merging with two of said second support straps at two spaced locations and also merging with two of said first support straps at additional two spaced locations, whereby each support section is positioned by four support straps, said second support straps extending directionally substantially opposite said first support straps, the second gap extending between the support sections,
    k) there being two like sets of said second support straps, adapted to be respectively associated with the infant's two ears and adapted to be respectively located at opposite sides of the infant's face when the chin support is worn, each of said second support straps having end extents that merge into a single top strap whereby two of said top straps are positioned in configuration for adjustable retention at a top head zone of the infant when the chin support is worn for simultaneous adjustment at said top of the infant's head to adjust the two sets of second support straps relative to the infant's ears when the chin support is worn, the chin support having two openings, each opening bounded on two sides by two of said second support straps thereby defining a width of each opening, each opening also being bounded on two other sides by one of said flexible support sections and one of said end extents thereby defining a length of each opening, wherein the length of each opening is longer than the width, and wherein the width of each opening is substantially constant throughout the length between said second support straps from said one of the flexible support sections and said one of the end extents,
    l) there being a laterally narrow, longitudinally elongated extent of said first gap formed between and sidewardly of said first flexible support straps, said first gap having tapering ends directed toward and spaced from said flexible support sections.

2. The chin support of claim 1 wherein the first flexible support straps are substantially shorter that the second flexible support straps such that the flexible support sections are adapted to be located substantially below ear level, at the sides of the infant's face when the chin support is worn.

3. The chin support of claim 1 wherein said top straps are configured for overlapping retention at the top head zone of the infant when the chin support is worn, equidistantly from said openings.

4. The chin support of claim 1 wherein said chin support consists essentially of soft, flexible material, having substantially uniform thickness throughout.

5. The chin support of claim 1 wherein each of said thin flexible support sections has uninterrupted overall lateral width substantially greater than the combined lateral widths of said first flexible support straps and said first gap.

6. The chin support of claim 1 wherein the two openings are at least partially bounded by the second flexible support straps and are longitudinally elongated having a substantially uniform width, to provide essentially non-interference with the infant's ears when the chin support is worn, said openings endwise elongated directionally between said flexible support sections and said second straps, said chin support having lateral width approximating the substantially uniform width of each of said openings.

7. A chin support for an infant comprising
    first flexible support straps including an upper strap portion and a lower strap portion, wherein the upper strap portion is adapted to extend laterally and with curvature between a lower lip zone and a chin of the infant when the chin support is worn and the lower strap portion is adapted to extend laterally and with cupping between the chin and a neck of the infant when the chin support is worn;
    a pair of flexible support sections disposed on oppose ends of the first flexible support straps, wherein adjacent ends of the upper strap portion and lower strap portion merge longitudinally endwise into each of the pair of flexible support sections, wherein the pair of flexible support sections are applicable to infant facial zones below ears of the infant and laterally to opposites sides of the chin when the chin support is worn;
    a first gap between the upper strap portion and the lower strap portion, wherein the first gap is laterally narrow and longitudinally elongated, having a crescent configuration and tapering endwise toward the flexible support sections;
    a pair of second flexible support straps extending from each of said pair of flexible support sections and forming an opening around each ear of the infant when the chin support is worn; and a pair of top strap extents formed by merging ends of each of said pair of second flexible support straps opposite the pair of flexible support sections, each of said pair of top strap extents having adhesive or a hook-and-loop fastener configured for adjustable retention at a top of the head of the infant when the chin support is worn, wherein each opening is bounded on two sides by said pair of second flexible support straps thereby defining a width of each opening, each opening also being bounded on two other sides by one of said pair of flexible support sections and one of said pair of top strap extents thereby defining a length of each opening, wherein the length of each opening is longer than the width, and wherein the width of each opening is substantially constant throughout the length between said pair of second flexible support straps from said one of said pair of flexible support sections and said one of said pair of top strap extents.

8. The chin support of claim 7, further comprising a second gap disposed between the flexible support sections along the lower strap portion, wherein one of the pair of flexible support sections is adjacent to an end of the second gap and another of the pair of flexible support sections is adjacent to an opposite end of the second gap.

9. The chin support of claim 7 wherein said top strap extents are configured for overlapping retention at the top head zone of the infant when the chin support is worn, equidistantly from said openings.

10. The chin support of claim 7 wherein said chin support consists essentially of soft, flexible material, having substantially uniform thickness throughout.

11. The chin support of claim 7 wherein each of said flexible support sections has uninterrupted overall lateral width substantially greater than the combined lateral widths of said first flexible support straps and said first gap.

12. The chin support of claim 7 wherein the openings are at least partially bounded by the second flexible support straps and are longitudinally elongated having a substantially uniform width, to provide essentially non-interference with the infant's ears when the chin support is worn, said openings endwise elongated directionally between said flexible support sections and said second straps, said chin support having lateral width approximating the substantially uniform width of each of said opening.

13. A chin support for an infant comprising first flexible support straps including an upper strap portion and a lower strap portion defining a first gap therebetween, said first gap applicable to a chin of the infant when the chin support is worn;

a pair of flexible support sections disposed on oppose ends of the first flexible support straps said pair of flexible support sections applicable to facial zones of the infant laterally to opposites sides of the chin when the chin support is worn;

a pair of second flexible support straps extending from each of said pair of flexible support sections, each pair of second flexible support straps forming an opening around each ear of the infant when the chin support is worn; and a pair of top strap extents formed by merging ends of each of said pair of second flexible support straps opposite the pair of flexible support sections, each of said pair of top strap extents having adhesive or a hook-and-loop fastener configured for adjustable retention at a top of the head of the infant when the chin support is worn, wherein each opening is bounded on two sides by said pair of second flexible support straps thereby defining a width of each opening, each opening also being bounded on two other sides by one of said pair of flexible support sections and one of said pair of top strap extents thereby defining a length of each opening, wherein the length of each opening is longer than the width, and wherein the width of each opening is substantially constant throughout the length between said pair of second flexible support straps from said one of said pair of flexible support sections and said one of said pair of top strap extents.

* * * * *